US008679401B2

United States Patent
Stull, Jr. et al.

(10) Patent No.: US 8,679,401 B2
(45) Date of Patent: Mar. 25, 2014

(54) MICROWAVE DISINFECTION AND STERILIZATION

(75) Inventors: Willis Don Stull, Jr., Lubbock, TX (US); Andreas Alfred Neuber, Lubbock, TX (US); Michel Todd Brashears, Wolfforth, TX (US); Mindy Malynn Brashears, Wolfforth, TX (US); Christine Alvarado, Iola, TX (US); J Chance Brooks, Wolfforth, TX (US); David E. Sharbutt, Lubbock, TX (US)

(73) Assignee: Microzap, Inc., Lubbock, TX (US)

( * ) Notice: Subject to any disclaimer, the term of this patent is extended or adjusted under 35 U.S.C. 154(b) by 741 days.

(21) Appl. No.: 12/837,257

(22) Filed: Jul. 15, 2010

(65) Prior Publication Data

US 2011/0014331 A1 Jan. 20, 2011

Related U.S. Application Data

(60) Provisional application No. 61/225,606, filed on Jul. 15, 2009.

(51) Int. Cl.
*A61L 2/00* (2006.01)
*A61N 5/00* (2006.01)
*A23C 3/07* (2006.01)

(52) U.S. Cl.
USPC ............... 422/21; 422/186.01; 250/455.11; 250/492.1; 426/62

(58) Field of Classification Search
USPC ............... 42/21, 186.01; 250/455.11, 492.1; 426/62; 99/451
See application file for complete search history.

(56) References Cited

U.S. PATENT DOCUMENTS

| | | | | |
|---|---|---|---|---|
| 4,634,992 A | * | 1/1987 | Brown | 330/47 |
| 5,049,362 A | * | 9/1991 | Baumgarten | 422/186.05 |
| 2009/0092708 A1 | * | 4/2009 | Alvarado et al. | 426/62 |

OTHER PUBLICATIONS

Klein, Eili, et al., "Hospitalizations and Deaths Caused by Methicillin-Resistant *Staphylococcus aureus*, United States, 1999-2005," Research:Emerging Infectious Diseases, www.cdc.gov/eid, Dec. 2007 vol. 13, No. 12, pp. 1840-1846.

* cited by examiner

*Primary Examiner* — Monzer R Chorbaji
(74) *Attorney, Agent, or Firm* — Chainey P. Singleton; Edwin S. Flores; Chalker Flores, LLP

(57) ABSTRACT

A method and apparatus comprising microwave radiation pulses to reduce a microorganism population in an object.

34 Claims, 12 Drawing Sheets

MICROWAVE DISINFECTION AND STERILIZATION

CROSS REFERENCE TO RELATED APPLICATIONS

This application claims the benefit of provisional patent application 61/225,606 filed Jul. 15, 2009 by the present inventors and the application is hereto incorporated by reference in its entirety.

STATEMENT REGARDING FEDERALLY SPONSORED RESEARCH OR DEVELOPMENT

Not Applicable

DESCRIPTION OF ATTACHED APPENDIX

Not Applicable

TECHNICAL FIELD OF THE INVENTION

This invention relates generally to the field of disinfection and more specifically to a novel method and apparatus for reducing a microorganism population on an object or material using a combination of thermal and non-thermal means, predominantly non-thermal.

BACKGROUND OF THE INVENTION

Disinfecting objects, materials, tissues and even body parts has been the source of study and research for centuries. Disease causing microorganisms flourish all around, but truly begin to wreak havoc when their numbers build around vulnerable populations of the elderly, immuno-compromised or the very young. In an attempt to address this danger, the Centers for Disease Control and Prevention ("CDC") produces an annual study describing various methods of sterilization and disinfection, and under what circumstances each method is appropriate. It is commonly recognized that to sterilize an object is to rid the object of essentially all live microorganisms. To disinfect an object is to rid the object of a percentage of live microorganisms. Described methods by the CDC to achieve sterilization, and even disinfection, include harsh chemicals, glass bead sterilizers, autoclaves and vaporized hydrogen peroxide. A constant struggle exists to achieve the highest level of microorganism eradication, while preserving the viability and characteristics of the underlying object, tissue or matter; using the least amount of energy, and having the least environmental impact.

Although the necessity for sterilization and disinfection encompasses virtually all industries, certain environments such as hospitals, nursing homes, daycares, schools and medical clinics are at especially high risk for microorganism spread and cross contamination. Professionals and scientists continually seek more effective, less expensive and more environmentally friendly ways to destroy or inactivate unwanted bacteria, molds, fungi and viruses.

Hospital and nursing home spread of destructive germs like the well-known *Staphylococcus aureus* cause significant cost, discomfort and extended suffering for patients already coping with underlying illness or disability. Patients affected by *Staph aureus* require expensive antibiotics, sometimes suffering additional side effects in the process. The growing migration of *Staph aureus* in recent years, followed by aggressive antibiotic treatment, has caused antibiotic resistant strains to evolve. One such strain, Methicillin resistant *Staphylococcus aureus* ("MRSA") is a bacterium that is resistant to a large group of antibiotics called the beta-lactams. This group includes the penicillins and cephalosporins. For patients with MRSA, physicians must often resort to treatment with Vancomycin, an extremely expensive and potent antibiotic. New "superbugs" have begun to emerge that, frighteningly, are resistant even to powerful Vancomycin. One such bug is known as Vancomycin Resistant *Enterococcus* or ("VRE"). The cost associated with fighting these "superbugs" and the toll on human life is mounting.

In 2007, the CDC estimated that the number of MRSA cases in hospitals doubled nationwide, from approximately 127,000 in 1999 to 278,000 in 2005. (Klein and Laxminarayan, 2007). They further estimated that annual deaths increased from 11,000 to more than 17,000. The preference is to prevent the contamination and cross contamination of harmful microbes, rather than attempt ever more aggressive means to treat patients affected by them. In that quest, hospitals have launched targeted campaigns to reduce the spread of all nosocomial infections, including MRSA and VRE. One obvious source of contamination is that of bed linens, washcloths and towels. Such items come into contact with copious amounts of bodily fluids and are exceedingly difficult and costly to fully disinfect. Current methods to sterilize hospital linens, such as steam or harsh chemicals, are expensive highly consumptive of energy and can be destructive to the fibers, shortening the lifespan of the linens.

Medical environments incorporate various levels of cleanliness depending on the object being cleaned. Sterilization is indicated for medical instruments or devices that enter the sterile tissues, the vascular system or where blood flows. As sterilization almost completely eradicates microorganisms, it has become the preferred method for cleaning objects that will be used invasively. (Guideline for Disinfection and Sterilization in Healthcare Facilities, 2008, CDC; Rutala and Weber). Disinfection is a less potent technique than sterilization and may be high level, mid level or low level, depending on the desired use of the object, its level of intended invasiveness and the corresponding potential for contamination in the human body.

Although sterilization can be achieved by use of harsh chemicals, irradiation, steam and other methods, certain disadvantages including high cost, high energy requirements, high intensity of time and labor and harmful chemical environmental effects may accompany each of these.

Our society is increasingly becoming a "throw-away" society. Part of the reason modern day services, and specifically medical services, are so expensive is due to this disposability factor. A vast number of small articles are used in daily treatments and thrown away due to concerns about the ability to thoroughly sanitize. A cost-effective way to safely and consistently sanitize these objects is needed.

Another cause for concern with regard to potentially harmful microorganisms is our food supply. A common theme in the news is the contamination of large scale crops by common pathogens such as *Salmonella* sp or *Eschericia Coli* sp. Often growers are forced to recall and dispose of contaminated crops, at a huge cost and societal waste. Decontamination would be a welcome alternative.

Contamination is not limited to human food supplies. Pet foods are often contaminated with microorganisms which can easily be transmitted to a human handling the food or accidentally ingesting it.

United States Patent Application 2009/0092708 previously discussed a method for using microwave radiation to extend the shelf-life of foods, however, the inventors therein utilized a continuous stream of microwave radiation lasting in duration of at least seven seconds to pretreat foods prior to packaging, far different from the repetitive pulse therapy and other novel method and apparatus disclosed herein.

Microwave radiation is typically thought to be unable to emit radiation waves in an even and consistent enough pattern to allow for reliable sterilization or disinfection. To achieve sterilization requires a 99-100% elimination of microorganisms, heretofore not reliably achievable by microwaves. Microwave radiation was recently suggested for use to sterilize mail of harmful organisms such as anthrax. The United States Postal Service, however, determined that microwave radiation, as currently understood, would be ineffective for mail sanitation, primarily due to its perceived inability to achieve reliable and even application.

A method and system is needed to reliably and efficiently sterilize food and non-food objects, at a reasonable cost, without altering the object's characteristics, further harming the environment or requiring large amounts of energy. Potential applications of such a novel technology run the gamut from ridding locker rooms of athlete's foot to sterilizing hospital linens to reducing microorganism populations in human, pet and stock animal food.

SUMMARY

In accordance with the present invention, a method and apparatus is provided for the sterilization and disinfection of food and non-food objects. Examples of objects that would be practical for this application include linens, towels, washcloths, rags, clothing, shoes, instruments, carpet, fabric, cloth, wood, plastic, glass, synthetic materials, paper, nutritional supplements, botanicals, herbal medicines, plants, minerals, oils, composite materials, building materials, fibers and upholstery, and even infected human or animal appendages, although potential uses are not limited to those described. The disclosed method and apparatus is also effective when used on fresh foods including but not limited to such items as fruits, vegetables, breads, meats, dairy products, spices, powders, crackers, liquids, plants, herbs, juice, extracts, oils, medicines, water, beverages, seafood, yogurt, nuts, seeds, honey, sugar, cereals, grains, jellies, processed foods, eggs and animal foods.

An objective of the disclosed invention is to achieve disinfection or sterilization of a food or non-food object quickly, efficiently and without adversely affecting the object's physical characteristics.

An objective of the disclosed invention is to achieve disinfection or sterilization of a food or non-food object without harming the environment.

An objective of the disclosed invention is to achieve disinfection or sterilization of a food or non-food object in a cost effective manner.

An objective of the disclosed invention is to achieve disinfection or sterilization of a non-food object or material, including eradication of difficult organisms such as methicillin resistant *Staph aureus*.

An objective of the disclosed invention is to achieve a more homogenous and uniform microwave signal on an object in a chamber.

An objective of the disclosed invention is to achieve uniform eradication of microorganisms in a food or non-food object using a combination of thermal and non-thermal effects, predominantly non-thermal.

An objective of the disclosed invention is to achieve disinfection or sterilization of food, including near eradication of difficult organisms such as *Salmonella* sp.

An objective of the disclosed invention is to achieve control of thermal effects by variable pulses (including repetitive and/or continuous pulses) of microwave radiation into a chamber to achieve an increased electrical field while controlling the energy into the chamber.

Other objects and advantages of the present invention will become apparent from the following descriptions, taken in connection with the accompanying figures, wherein, by way of illustration and example, an embodiment of the present invention is disclosed.

BRIEF DESCRIPTION OF THE DRAWINGS

The figures constitute a part of this specification and include exemplary embodiments to the invention, which may be embodied in various forms. It is to be understood that in some instances various aspects of the invention may be shown exaggerated or enlarged to facilitate an understanding of the invention. To enable more thorough understanding of the features and advantages of the present invention, reference is now made to the detailed description of the invention along with the accompanying figures in which.

DETAILED DESCRIPTION OF THE PREFERRED EMBODIMENTS

Figure 1:
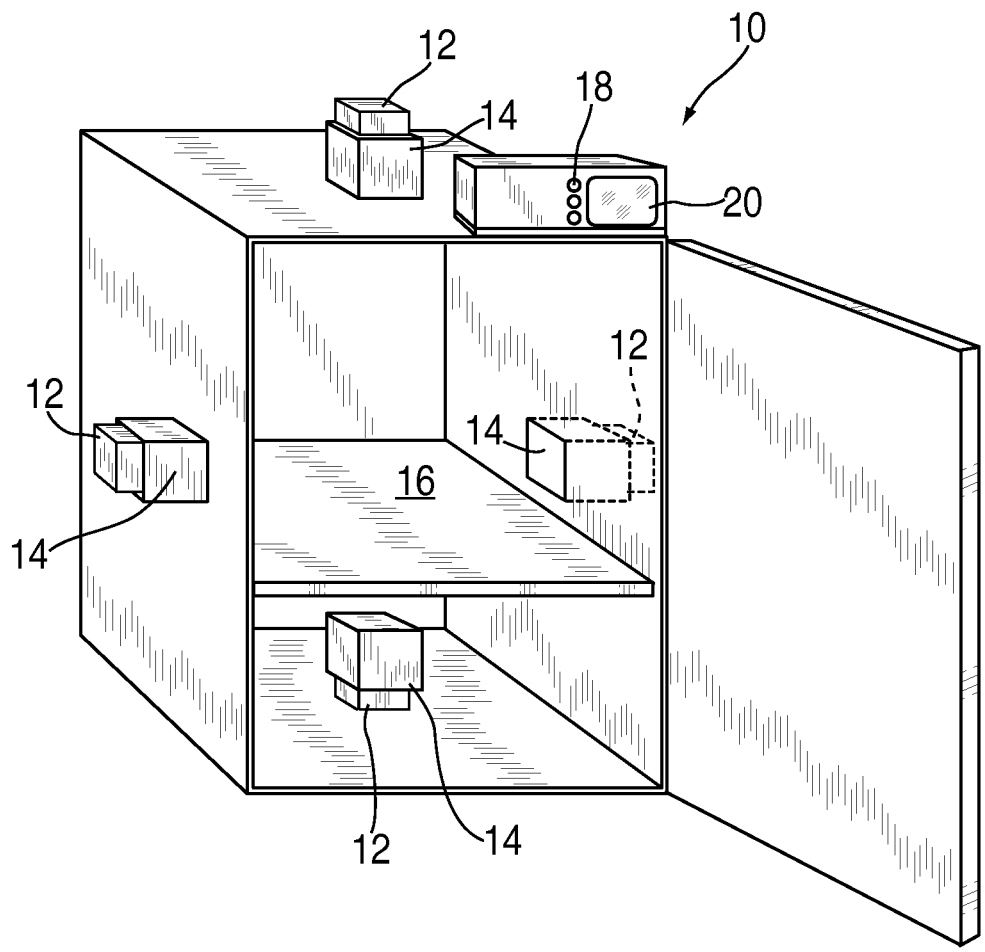
FIG. 1 depicts an apparatus in accordance with the preferred embodiment of the disclosed invention.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

"Object or objects" may comprise a variety of articles, materials, tissues or substances and may include linens, uniforms, towels, washcloths, fabrics instruments, any food product for human or animal consumption or any such item for which microwave radiation would serve as a practical and effective means to achieve the purposes described herein. "Microorganism" as defined herein may include bacteria, fungi, molds, prions and viruses.

Breakthrough technology has recently come to light with capabilities to sterilize objects in a predominately non-thermal manner. Avoiding heat as the primary means of sterilization is important because it saves energy and avoids altering physical characteristics of the object.

In 2004, nosocomial infections were the fourth leading cause of death in the United States, right behind stroke, cancer and heart disease. Although noninvasive objects such as sheets, towels and washcloths are not required to be sterilized, certainly achieving a higher level of disinfection in these commonly used items would decrease the incidence of nosocomial infections, much in the way hand washing has done so. Especially for the vulnerable population of elderly, ICU patients, and premature infants, every possible way to decrease microorganism spread saves lives and dollars.

Destruction of microorganisms during microwaving is known to be possible by thermal effects, such as microwaving an object a sufficient length of time for the object to have a raised temperature sufficient to kill the microorganisms. Relying, however, on thermal kill for sterilization of objects is inefficient, inconsistent, uses too much energy and can result in undesirable secondary effects. For example, although it may be possible to disinfect a kitchen towel by placing it in a domestic microwave, one would need to keep it in the microwave for at least two minutes and even then, one would not be guaranteed consistent eradication, as the towel may still have hot and cold spots. Two minutes of microwave energy to poorly disinfect one towel is furthermore an inefficient use of energy.

The inventors, however, have developed a method and apparatus by which microorganisms, even strong microorganisms such as methicillin resistant *Staph aureus*, can be virtually eliminated from an object using pulses of microwave radiation that result in predominately non-thermal kill of the microorganisms.

Four theories describe non-thermal kill as being accomplished by selective heating, electroporation, cell membrane rupture and electromagnetic field coupling or a combination of these. The disclosed invention utilizes both thermal and non-thermal effects to achieve very high elimination of microorganisms on a contaminated object.

Traditionally, directional microwaves interact with dielectric materials to generate heat by the agitation of molecules in an alternating electromagnetic field. Objects or microorganisms with high water or carbon content absorb the microwave radiation more effectively and are thus more susceptible to its effects.

Provided the unwanted microorganism has a water or carbon content, such a microorganism could be eliminated from even a non water containing or carbon containing object, using the disclosed method and apparatus. Many of the traditional methods of sterilization incorporate hot water, either in the form of boiling water or steam, such as autoclaving. Although effective, these methods are energy expensive to generate.

Conventional domestic microwaves rely on rotary movement to achieve heating and cooking which results in uneven distribution and untreated areas. This is a major reason that microwave sterilization has heretofore not been a recognized mode of sterilization or high level disinfection. In recent years, concerns have arisen that home microwaves may not even be safe for preparing certain processed foods, such as pizzas or other meals, due to the cold spots that persist after cooking. Labels on many processed foods now advise that microwaving is not an option for cooking the food. The disclosed method and apparatus embodies techniques to ensure a more homogenous signal, uniformly distributed throughout the object for consistent reduction of microorganisms.

The present invention incorporates a novel method of efficiently reducing the population of microorganisms on an object or material by using various types of movement, manipulating the waves and by varying pulses of microwave radiation.

In addition to molds, fungi and viruses, microorganisms that can be reduced using the disclosed method and apparatus include Gram-positive and Gram-negative bacterium including but not limited to *Staph aureus*, methicillan resistant *Staph aureus, Eschericia Coli, Salmonella* sp, *campylobacter* sp, *listeria monocytogenes, clostridium* sp, *shigella* sp, *staphylococcus* sp.

Turning to the figures, FIG. 1 illustrates the described method and apparatus in the configuration of a four sided chamber 10 shown here with four magnetrons 12, one on the top, one on the bottom and one on each opposing side. The number of magnetrons may vary from as few as one to as many as eight or more and the magnetrons may be located in a variety of locations on the apparatus, including mounted on the door, provided a signal is achieved that is as uniform as possible. In this embodiment, the object may rest on a stationary platform 16 or may travel through the apparatus on a conveyor belt. Unlike in conventional home microwaves where the turntable or platform is positioned on the base of the inside of the unit, in FIG. 1 the platform 16 is raised, serving to ensure that the microwave feed strikes the object as uniformly as possible from both the top and bottom. The object is placed on the platform 16 and receives pulse microwave treatment as programmed (pulse duration, pulse period, microwave mode distribution) for the specific type of treatment desired, for example sterilization or high level disinfection using primarily non-thermal means or a combination of thermal and non-thermal means. Pulse duration is the length of time each pulse lasts. Pulse period is the length of time the object is treated with pulses. The microwave mode distribution refers to the way in which the microwaves are manipulated, for example, horizontally, vertically, through a slot radiator, or other means, and is also determined by the microwave resonances of the chamber.

The chamber of the apparatus, when designed with specific dimensions and ratios (for example, designing the chamber to have unequal height, width and depth, avoiding a square or cubed configuration) further assists with improvements in uniform distribution of the microwave radiation throughout the object, generating a larger number of microwave modes as they resonate in the chamber within the frequency bandwidth of the magnetron source, and, as a result, achieving a more uniform treatment.

At the top right of the apparatus are pictured the controls 18 and the power supply 20.

Figure 2:
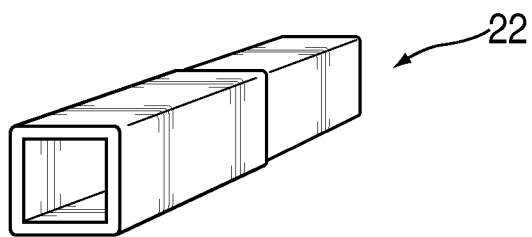
FIG. 2 depicts a telescoping waveguide in accordance with an embodiment of the disclosed invention.

Each magnetron 12 is accompanied by one or more waveguides 14 in order to direct and manipulate the waves. The waveguide may be a telescoping waveguide 22 as pictured in FIG. 2. The telescoping waveguide 22 allows the user to direct and target the waves. As the sliding waveguide 22 is withdrawn into its chamber it becomes shorter and closer to the magnetron 12, yet farther from the object to be treated, resulting in less intense power directed to the object. The sliding waveguide 22 may conversely be slid forward in its chamber, drawing closer to the object and directing the wave power in a more targeted fashion to the object.

Figure 3:
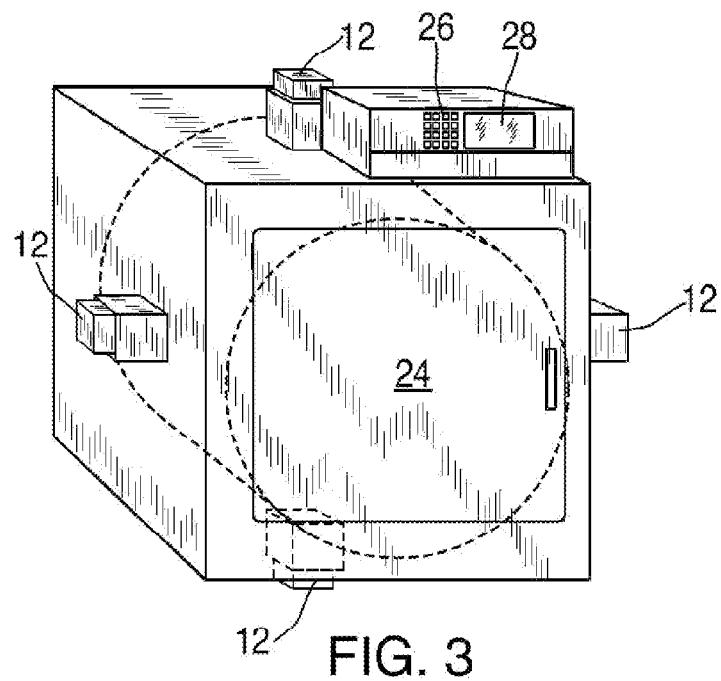
FIG. 3 depicts an apparatus in accordance with an alternative embodiment of the disclosed invention.

FIG. 3 depicts the apparatus having a box configuration but with a cylinder type tumbler drum 24 inside. The apparatus shows four magnetrons 12 although a different number may be used as well. The tumbler drum 24 enables mobilization of the targeted object, achieving more uniform treatment. The tumbler drum 24 may incorporate variable speed controls 26, allowing the user to adjust the speed based on the object. The power supply 28 is also depicted.

The inventors discovered that pulses of microwave radiation, rather than a steady signal, were effective in promoting microorganism reduction without a substantial increase in temperature.

Figure 10:
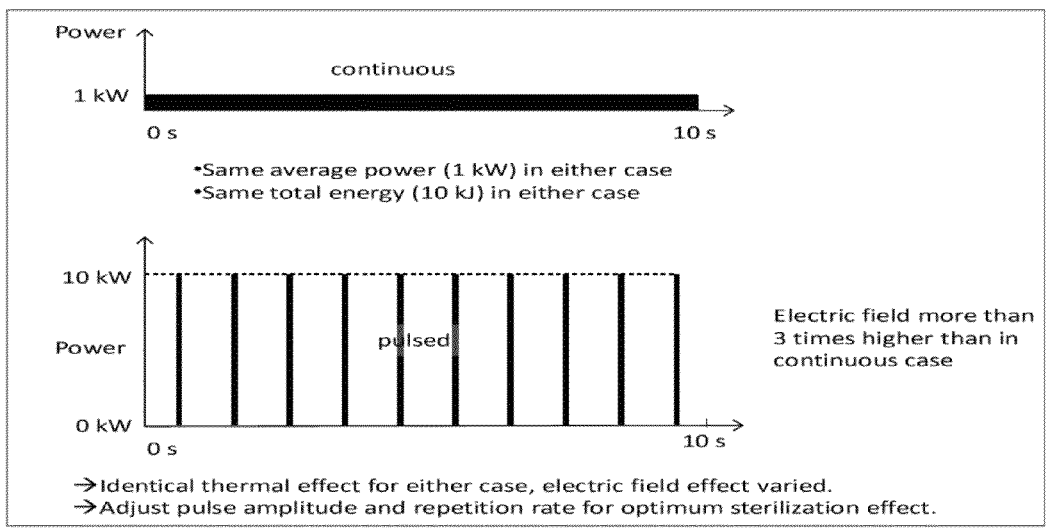
FIG. 10 is a table in accordance with an embodiment of the disclosed invention.

As FIG. 10 reflects, the electric field can be amplified while maintaining the same temperature of the treated material by utilizing microwave pulses rather than continuous microwave radiation. As an example, using an average power of Pave=1 kW, which leads to a certain temperature increased determined by the treatment length. For a 10 second treatment time this results in an energy of Etreat=Pave*10 s=10 kJ. The same energy can be put into the treatment system if the microwave source is pulsed with, for instance, 20 kW pulses, each pulse 0.05 second long (energy in a single pulse 1 kJ). If the pulses are then spaced 1 second apart one gets a total energy of 10 kJ within 10 seconds, the same as in the continuous case of 1 kW power. This is merely an example and a variety of combinations may be used. However, in the example, the peak electric field was roughly 4.5 times larger in the pulsed case (electric field scales with the square root of the pulsed power), making electroporation and other direct cell attack mechanisms more pronounced. With this approach, the thermal effect is kept constant and the electric field contribution is increased. The combination of thermal and non-thermal attack can then be tailored for the specific object or materials to be treated.

These results further confirm that with pulsed microwave treatments, one can keep the thermal effect constant while increasing the electric field contribution, increasing non-thermal kill by electroporation and other direct cell attack mechanisms. This is important as the non-thermal kill tends to rid the object of the unwanted organisms without affecting the physical characteristics of the object. It is also important because the short duration of treatment means practical application from an industrial standpoint.

Varying polarization (including horizontal, vertical, telescoping waveguide and the use of a slot radiator) may be used to specifically direct the waves to achieve even more signal uniformity. The object or material may be exposed to repetitive pulses of microwave radiation, each pulse having a duration and period adjusted such that the average power equals to a value preset by the user.

As an example, the user may preset 1 kW average power for a system with a 10 kW magnetron. The user may choose 0.1 second pulse duration (10 kW*0.1 s=1 kJ per pulse). The pulse period may be equal to 1 kJ/1 kW=1 s. In other words, the 10 kW magnetron is fired every one second with 0.1 s pulse duration. Other combinations are possible as well, such as 5 kW magnetron fired every 0.5 s with 0.1 s pulse duration or 10 kW magnetron fired every 0.5 s with 0.05 s pulse duration.

Expressed as an equation this would be reflected as follows:

$$T_{period} = P_{peak} * T_{duration} / P_{average}$$

In an embodiment, the total treatment duration is also set by the user. $T_{treatment} = T_{period} * N$ with N being the total number of pulses selected. The total energy fed into the chamber is Etreat=$P_{average}$*$T_{treatment}$ and as such the same for all cases. In the extreme case for $T_{period} = T_{duration}$, the magnetron is continuously driven for the treatment duration; that is a single pulse with $T_{treatment}$ duration.

Another way of representing the methods employed herein is by reference to a "Duty Cycle", which is the dimensionless ratio of pulse duration over pulse period and is illustrated by the equation: Duty Cycle=$T_{duration}/T_{period}$ One kHz is a pulse every millisecond (100 kHz every 0.01 ms) and a mHz (milli Hz) is a pulse every 1000 seconds.

Figure 4:
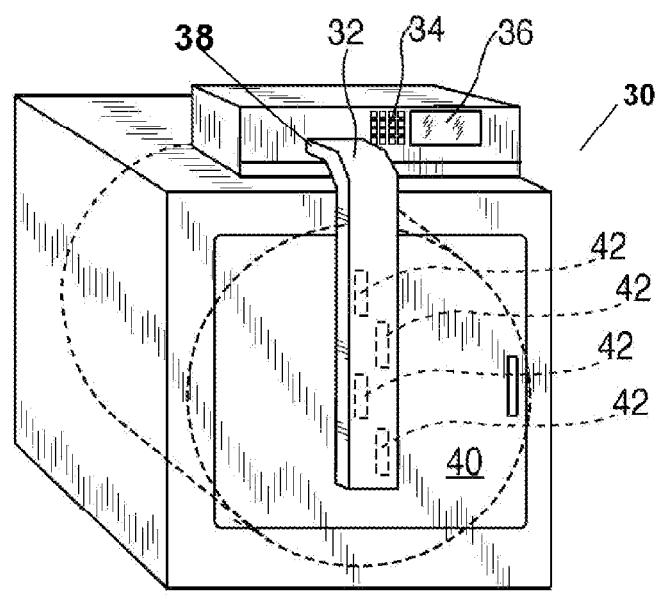
FIG. 4 depicts an apparatus in accordance with an alternative embodiment of the disclosed invention.

FIG. 4 reveals an alternative embodiment of the apparatus, utilizing a cylinder type tumbler drum 30 configuration. In this example, the magnetron head 38, controls 34 and power supply 36 are mounted to the top of the chamber. The waveguide 32 passes over the front of the door 40 and the holes of the slot radiator 42 are indicated on the waveguide backside. The pulses of microwave radiation are dispersed more evenly on the object by means of the slot radiator holes 42.

Figure 5:
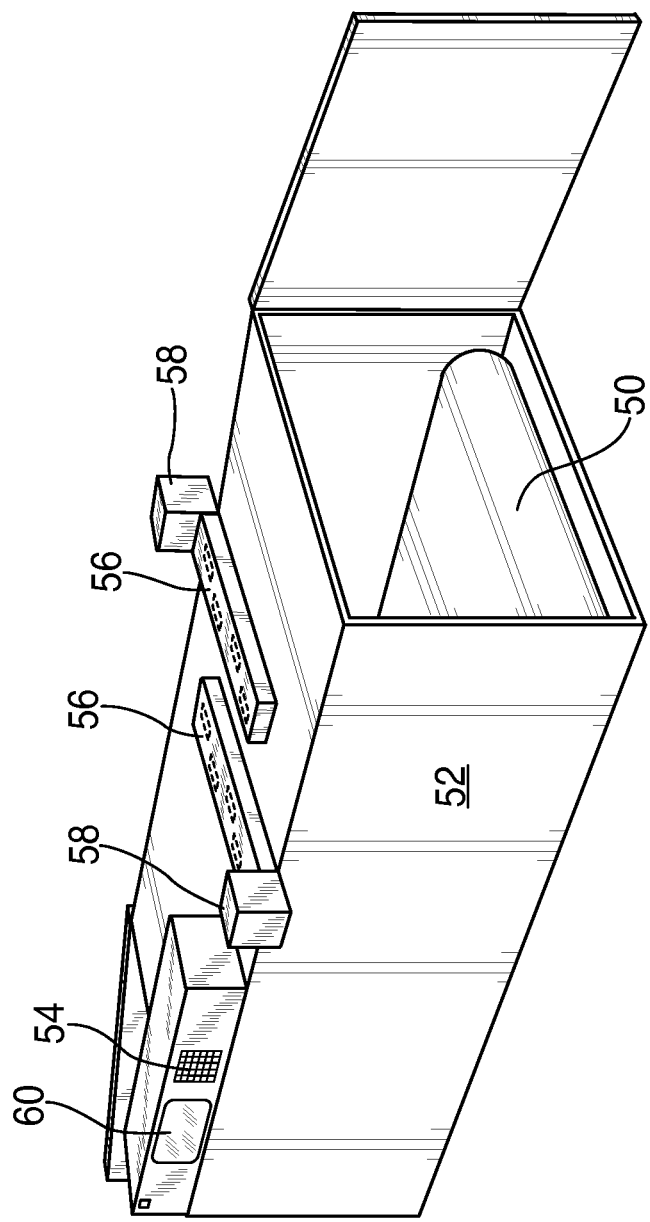
FIG. 5 depicts an apparatus in accordance with an alternative embodiment of the disclosed invention.

FIG. 5 reveals an alternative embodiment, namely a conveyor belt 50 configuration. In this figure, one notes the rectangular shape of the chamber 52, although other shapes may be utilized. Mounted on top of the chamber are the control panel 54 for operation of the apparatus, two microwave slot radiators 56, two magnetron head(s) 58, and the power supply 60. The slot radiator and the conveyor belt together enable even greater homogeneity of the electric field distribution. The conveyor belt 50 travels through the length of the chamber 52, enabling movement of the object, further improving uniformity of the treatment.

In operation, the object is placed on the conveyor belt, the chamber closed in some fashion (door, water curtain or other means) and the treatment is initiated. The operator programs the controls for the duration and period of pulses desired, depending on the type of object and treatment required. The object passes through the chamber on the conveyor belt, receiving pulses of microwave radiation, quickly becoming disinfected, without a concurrent high increase in temperature.

Figure 6:
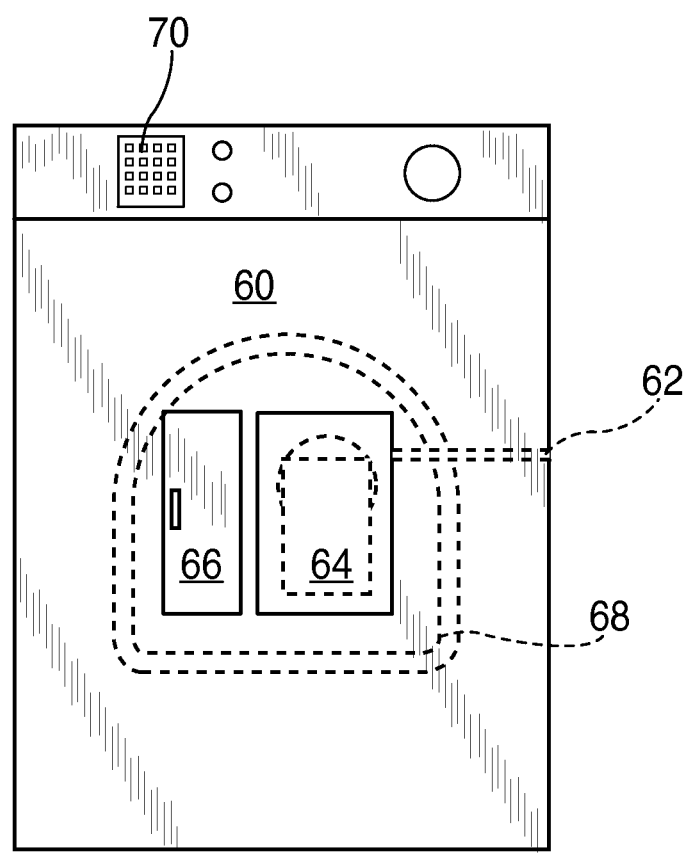
FIG. 6 depicts an apparatus in accordance with an alternative embodiment of the disclosed invention.

FIG. 6 is an alternative embodiment reflecting a configuration where the main components are affixed to the inside of the door of the chamber 60. The illustration reveals a high voltage conduit 62 for safety purposes, the magnetron waveguide assembly 64, a copper access door 66 (although other materials may be used) and copper mesh 68 and/or EMF gaskets were used over the joint of the main door to further shield EMF leakage. Controls 70 are depicted on the top front of the unit.

Figure 7:
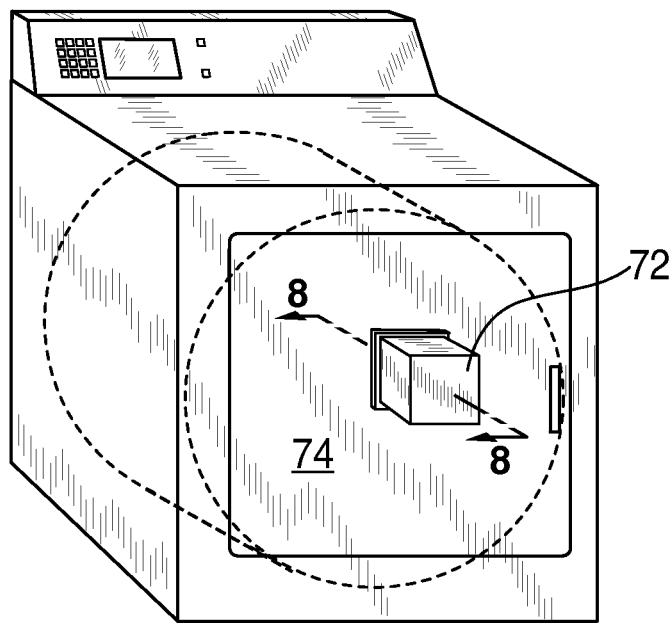
FIG. 7 depicts an apparatus in accordance with an alternative embodiment of the disclosed invention.

FIG. 7 illustrates an alternative embodiment of tumbler drum configuration with the microwave assembly 72 mounted on the outside of the door 74. In this embodiment the object or material can be placed in the chamber to achieve both drying and microwave disinfection simultaneously or just microwave disinfection/sterilization.

Figure 8:
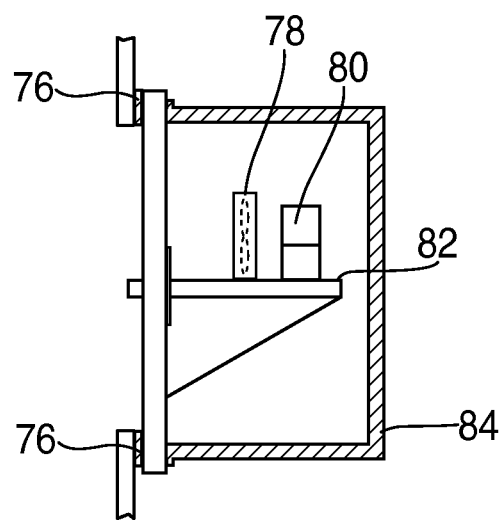
FIG. 8 depicts an apparatus in accordance with an alternative embodiment of the disclosed invention.

FIG. 8 shows a cut away section of the inside of this microwave assembly 72, showing the EMF gasket 76, a cooling fan 78, the magnetron 80, the waveguide 82, and a metal cover 84 encircling the assembly to prevent EMI leakage and ensure personnel safety (copper is used in the prototype but other metals may be used).

The cooling fan is pictured to cool the magnetron, as is common in the art with regard to microwaves. Cooling can also be accomplished with water flow for higher average power microwave source.

Figure 9:
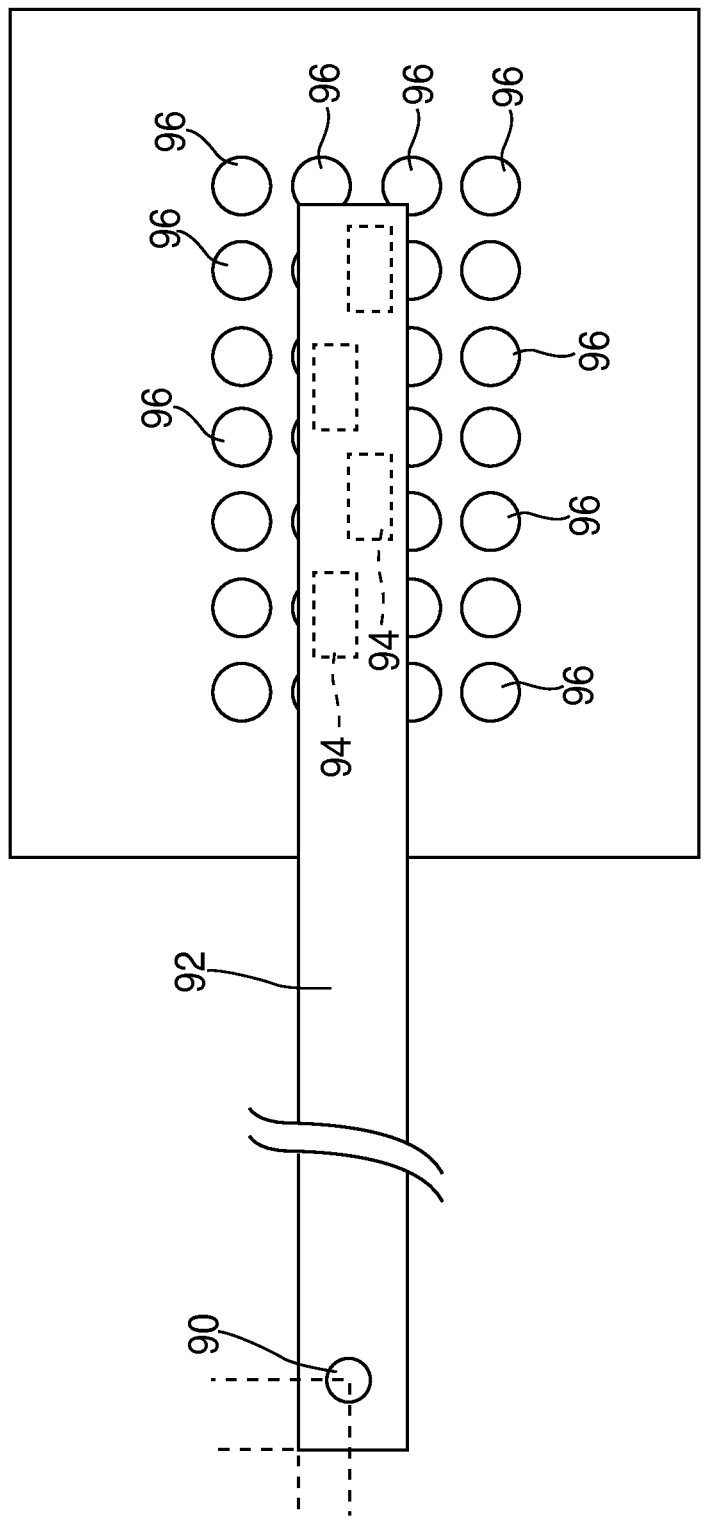
FIG. 9 depicts representation of a slot radiator in accordance with the preferred embodiment of the disclosed invention.

FIG. 9 illustrates the microwave feed 90 into a waveguide 92 having radiating slots 94, traveling over cups 96 of liquid to be treated. Each end of the waveguide 92 is closed, forcing the microwave radiation through the radiating slots 94. This method enables improved signal homogeneity.

Testing by the inventors revealed that various modifications can be made to the apparatus in order to improve the homogeneity of the signal to ensure consistent reduction of the microorganisms. Steps employed to improve signal uniformity included moving the object during treatment, designing the chamber in certain dimensions and sizes, varying the pulses to increase the electric field contribution without increasing temperature, and manipulating the waves to improve homogeneity. Metallic reflectors and various magnetron angles were also employed in testing as alternative embodiments to improve signal uniformity.

Moving the object during treatment is accomplished by means of a tumbler or a conveyor belt although any reasonable means to accomplish object movement during treatment may be appropriate.

With regard to chamber sizes, it is beneficial to avoid a square box configuration. A chamber having width, height and depth of unequal sizes was found to further improve the signal homogeneity. This reduces the probability of producing degenerated microwave modes which could lead to "cold spots" or poorly treated areas on the object.

When manipulating the waves, it was found that the preferred embodiment employed a waveguide length from end to end of n*lambda/2, (with lambda representing the wavelength inside the utilized WR284 waveguide of 17.35 cm) for tested frequency of 2.45 GHz magnetrons and n=whole integers, 1, 2, 3, 4, to infinity. Other waveguides or other frequencies may be used as well resulting in different wavelengths. A slot radiator on the waveguide, a concept adapted by the inventors, was found to have a benefit in generating a more homogeneous electric field distribution, making the treatment more uniform throughout the object.

Example 1

Treatment of Fabric

Hospital linens are continually in contact with bodily fluids and tend to be a rampant breeding ground for microorganisms. Microwave radiation that is homogeneously distributed and can be controlled in such an automated manner as to deliver only the precise energy needed to sterilize the object is a cost effective and reliable way to decrease nosocomial infections.

Figure 11:
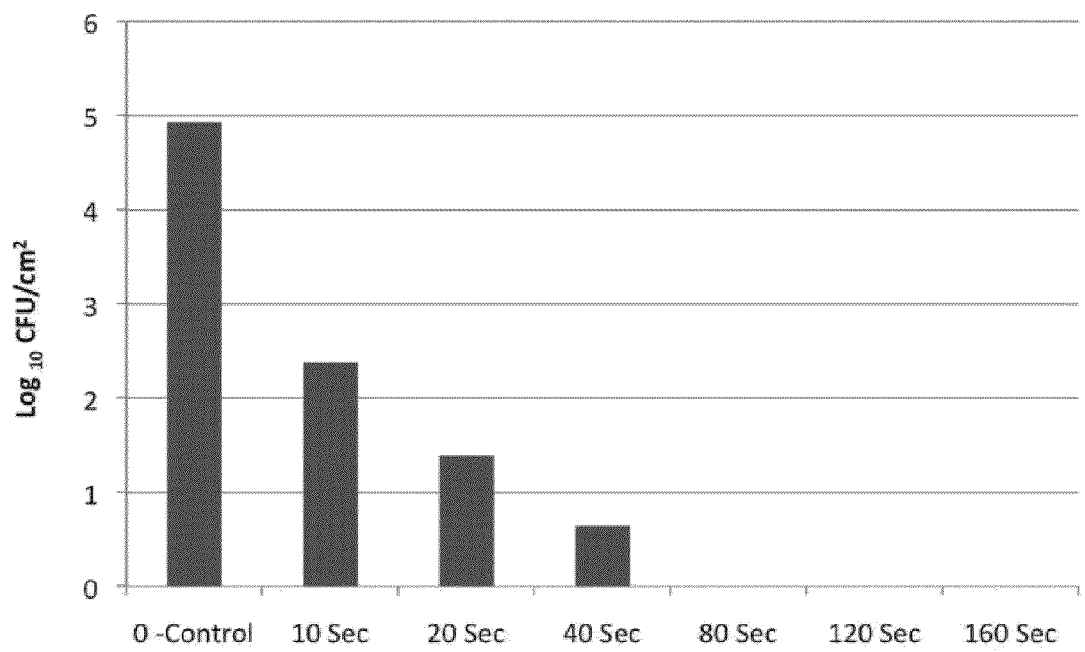
FIG. 11 is a bar graph in accordance with an embodiment of the disclosed invention.

FIG. 11 is a bar plot that shows the decline in the MRSA population from an initial MRSA count in MRSA inoculated cotton bedsheets of about 5 log 10 cfu/cm2 decreased to 0.6 log 10 cfu/cm2 after a 40 second microwave treatment.

The plot also reveals a reduction from 5 log 10 cfu/cm2 to 0 log 10 cfu/cm2 after an 80 second treatment. The difference between a 5 log 10 cfu/cm2 to a 0.6 log 10 cfu/cm2 count represents a greater than 99.99% reduction in the MRSA population. This indicates the 40 second microwave treatment of cotton fabric to be very effective in eliminating MRSA, and the 80 second microwave treatment to render near 100% eradication. Full beamwidth and a microwave frequency of 2.45 GHz, a frequency commonly utilized in the United States for industrial applications was used for this study, although certainly one skilled in the art will recognize that other frequencies, pulses and variables may be used to achieve the desired results.

In testing, the temperature of the object was never above 70 degrees Celsius, far below the threshold of a pure thermal kill for most microorganisms (approximately 120 degrees Celsius). Yet the data reflected a 5 log reduction (99.999%) in some studies and a 1 to 2 log reduction (90-99%) in others, revealing a very high kill and validating that predominately non-thermal effects are causing the kill. Thus the disclosed method and apparatus enables the destruction of microorganisms by microwave therapy even when the object is dry. An alternative embodiment is a cylinder type tumbler drum embodiment, similar to a clothes dryer, however having intermittent microwave energy.

Testing by the inventors revealed that when comparing placing the object to be treated on in a stationary position in the chamber versus tumbling, the fixed swatch had higher temperature readings, reflecting more energy into the object, however it also revealed a lack of homogeneity as seen by the variations identifying hot and cold spots. The tumbled object displayed a lower overall temperature but more uniform temperature distribution, thus more homogenous.

Example 2

Cantaloupe, Jalapeno Peppers, Dog Food, and Peanuts Inoculated with *Salmonella* and Treated In this controlled experiment, fresh cantaloupes were obtained from local grocery store with no noticeable blemishes. The cantaloupes were allowed to return to room temperature overnight. Each cantaloupe was submerged into a 3 strain *Salmonella* inoculum (4 Liters) and agitated by stirring with a glove-covered hand for 5 minutes to ensure uniform inoculation. Cantaloupes were placed on sterile stainless steel drying racks under a bio-safety cabinet for 1 hour to allow for drying. Untreated cantaloupes were subject to analysis for initial level of contamination of *Salmonella*.

Treatments were: Control (no treatment); 1 minute, 30 seconds stationary; 1 minute, 45 seconds stationary; 2 minutes—1 minute stationary: 1 minute (turning at mid point); 3 minutes—1 minute, 30 seconds stationary: 1 minute, 30 seconds (turning at mid point). To enumerate attachment of *Salmonella*, a stainless steel corker unit was utilized to produce rind plugs 22 mm in diameter with an external rind surface area of 3.80 cm$^2$. An even amount of core samples were taken from the two halves (10-15 rind samples taken per half of the cantaloupe)

Figure 12:
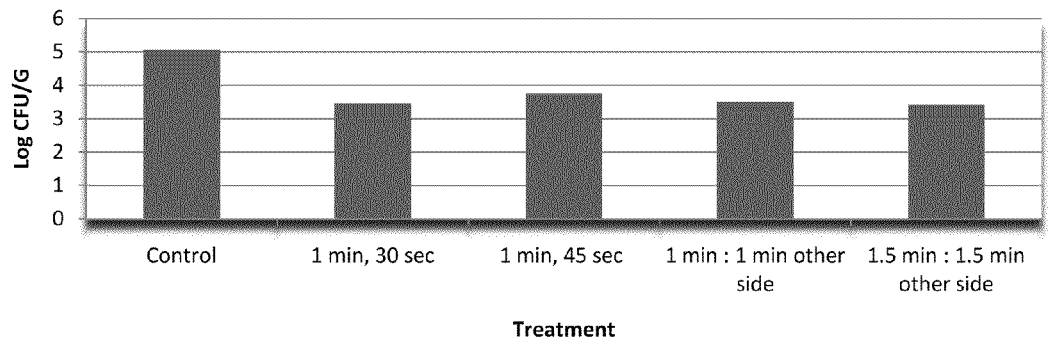
FIG. 12 is a bar graph in accordance with an embodiment of the disclosed invention.
Figure 12:
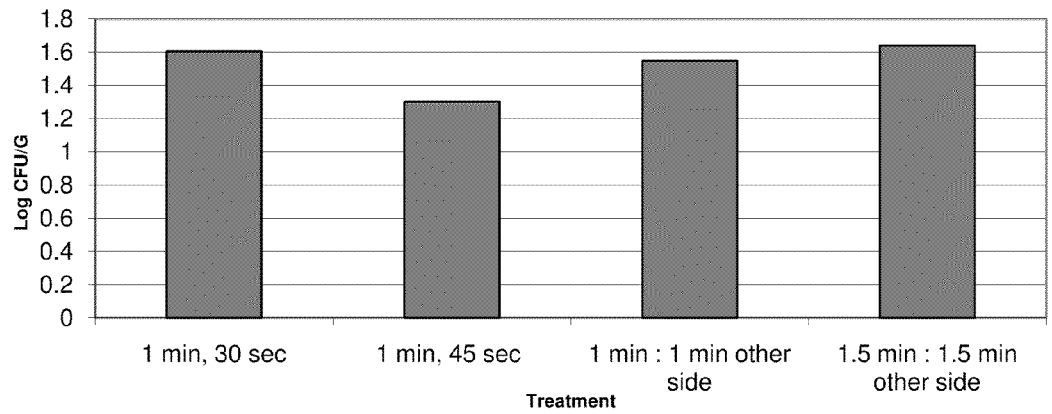

Internal flesh sample that adhered to the rind samples were trimmed off using a steel knife. Random plugs were selected to equal 25 grams (~20-30 rind samples) and blended with 75 ml of buffered peptone water in a blender at level 5 for 1 minute. Serial dilutions were performed and plated on XLD. The results of this test are reflected in FIG. 12.

Figure 13:
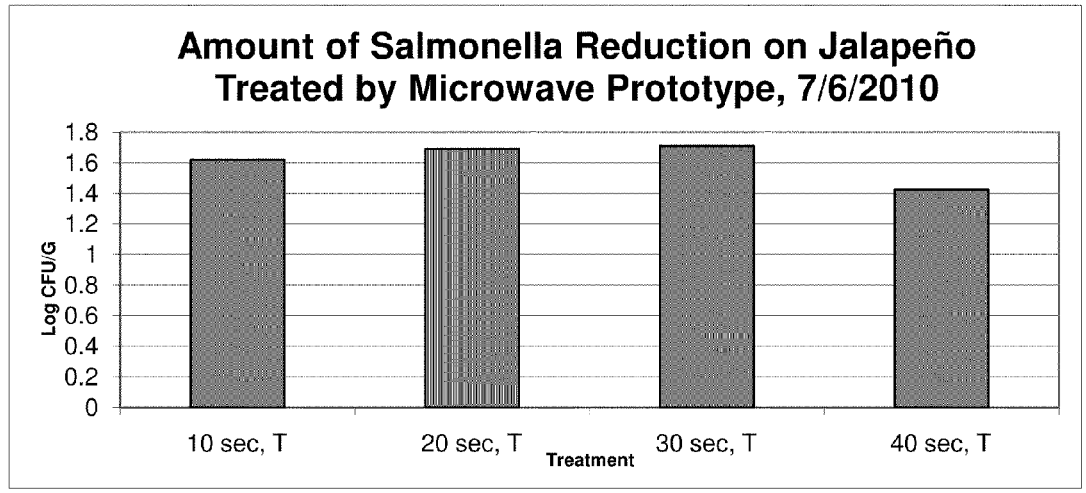
FIG. 13 is a bar graph in accordance with an embodiment of the disclosed invention.
Figure 13:
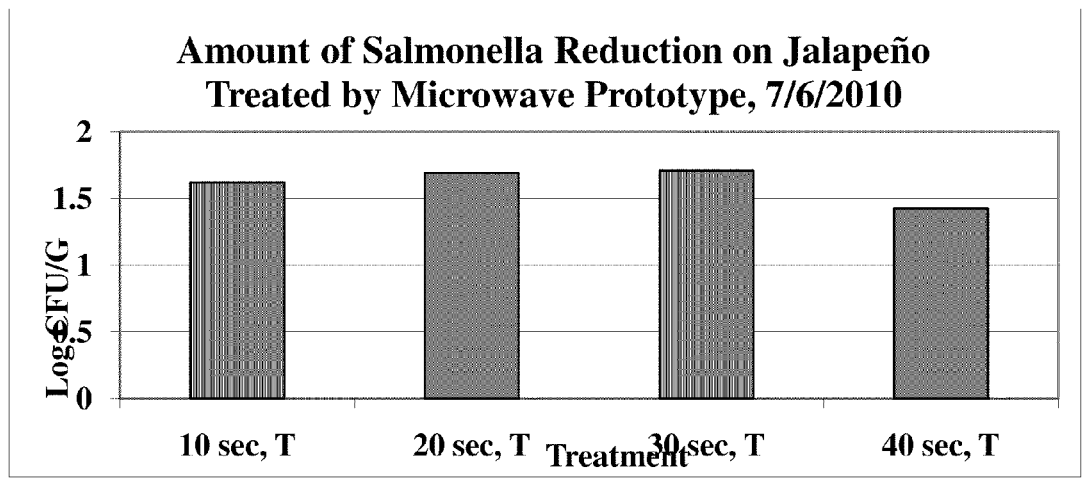

Next, jalapeno peppers were obtained from the local grocery store with no noticeable blemishes. The Jalapeno peppers were placed into a poultry rinse bag and submerged into 1 liter of a 3 strain *Salmonella* inoculum (1 Liter). The bag was agitated by swirling for 2 minutes to ensure uniform inoculation. Jalapeno peppers were placed on sterile stainless steel drying racks under a biosafety cabinet for 1 hour to allow for drying. Each jalapeno pepper was placed individually into a new stomacher bag. Treatments were: 10 seconds, 20 seconds, 30 seconds, and 40 seconds. To enumerate attachment of *Salmonella*, add 75 ml of BPW to each stomacher bag with 1 jalapeno pepper and agitation occurred for 5 minutes. Serial dilutions were performed and plated on XLD. Results are reflected on the bar graph of FIG. 13.

Figure 14:
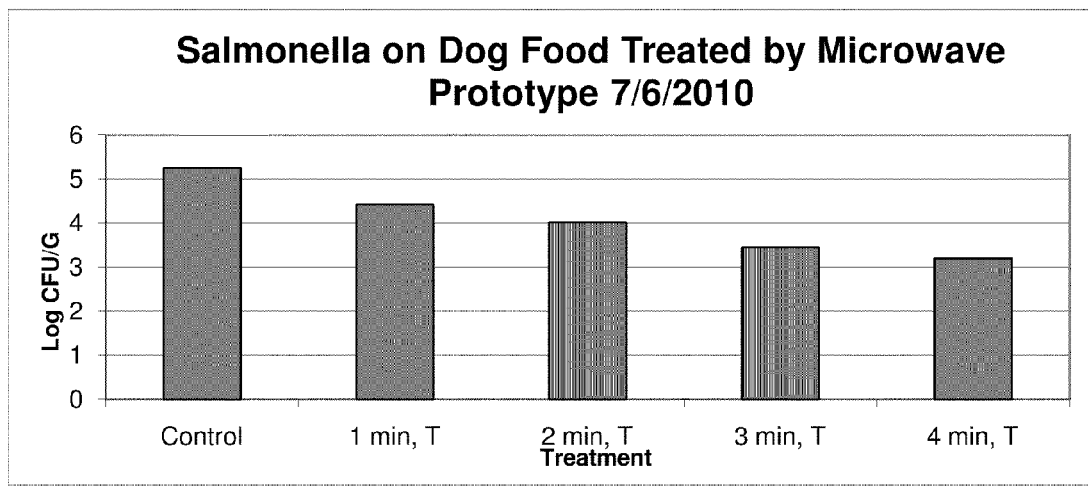
FIG. 14 is a bar graph in accordance with an embodiment of the disclosed invention.
Figure 14:
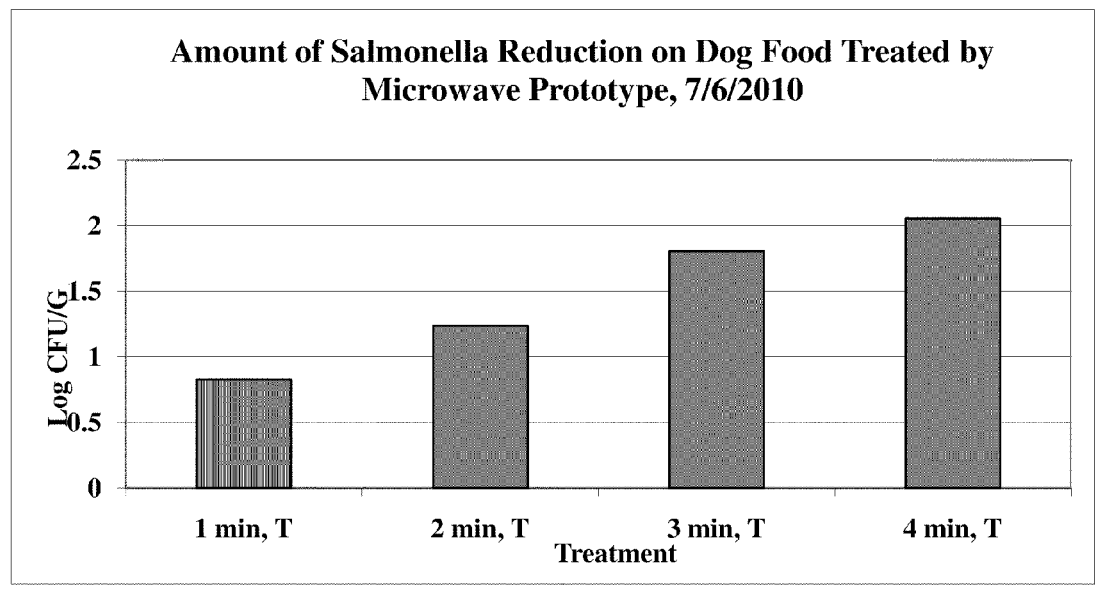
Figure 15:
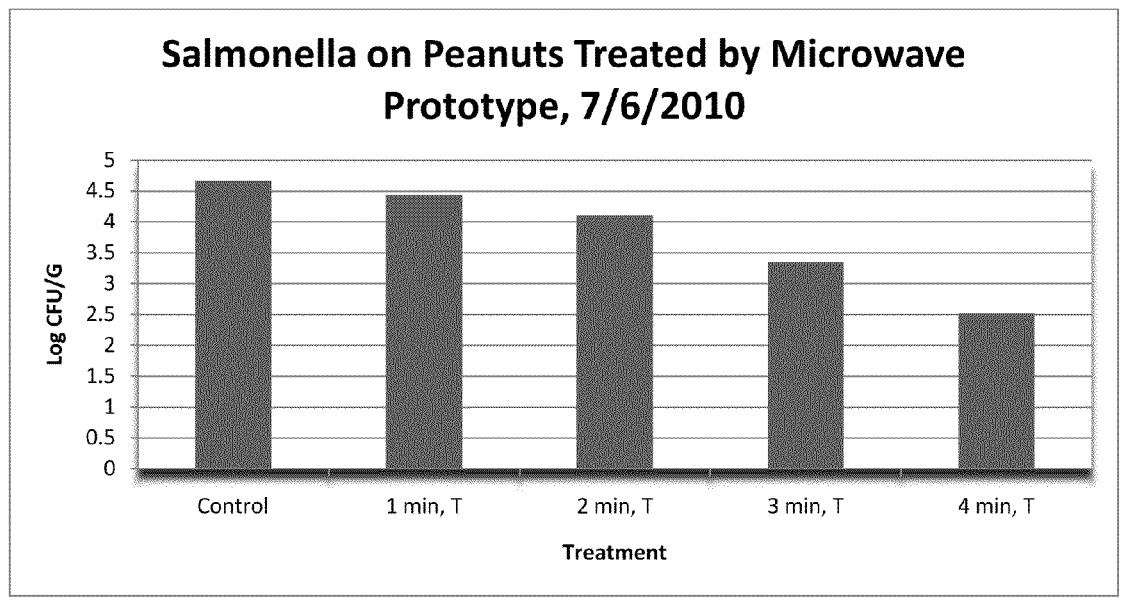
FIG. 15 is a bar graph in accordance with an embodiment of the disclosed invention.

Last, dog food and peanuts were obtained from the local grocery store and were autoclaved on a dry cycle. The dog food/peanuts were inoculated by placing between 250-300 grams of dog food/peanuts into a poultry rinse bag containing 1 liter of *Salmonella* inoculums. The bag was agitated by swirling for 1 minutes to ensure uniform inoculation. The dry dog food/peanuts were placed onto sterile stainless steel drying racks under a biosafety cabinet for 1 hour to allow for drying. 25 grams of inoculated dog food/peanuts were added into new stomacher bags. Treatments occurred in the new stomacher bags. Dog Food and Peanut Treatments were: 1 minute, 2 minute, 3 minute, and 4 minute and all were tumbled. To enumerate attachment of *Salmonella* dog food/peanuts, 75 ml of Butterfields Phosphate Buffer was added to each stomacher bag with 25 grams dog food/peanuts and agitation occurred for 5 minutes. Serial dilutions were performed and plated on XLD. The results of the dog food studies are reflected on FIG. 14 and the peanuts are shown on FIG. 15.

One advantage of the disclosed invention is that microwaves are much less harmful to the environment than harsh chemicals. The radiation waves emanating from a microwave, if any, dissipate rapidly a short distance from their source.

Science has periodically attempted to incorporate microwave technology for use in treating cancers or tumors. Difficulties arise in terms of failure of microwave irradiation to penetrate deeply enough without harming surrounding tissues. Use of microwave technology to treat bodily appendages affected by MRSA is yet unknown in the prior art. Based on the methods disclosed herein describing controlling variables of the microwave, it is possible that the described method could be used for such application, using very short pulses at high power.

It is to be understood that the embodiments disclosed herein are shown for illustrative purposes and are not intended to be construed as limitations of the disclosed method and system. Those skilled in the art will recognize or be able to ascertain in the course of routine experimentation, that variations and equivalents of the embodiments may be undertaken without departing from the scope of the invention.

The publications referenced herein are indicative of the level of skill of those skilled in the art to which the disclosed method and system applies.

Certain terms are used throughout the description to refer to particular method components. As one skilled in the art will appreciate, design and manufacturing companies may refer to a component by different names. This document does not intend to distinguish between components that differ in name but not function.

The terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other intermediate devices and connections. Moreover, the term "method" means "one or more components" combined together. Thus, a method can comprise an "entire method" or "sub methods" within the method.

The use of the word "a" or "an" when used in conjunction with the word "comprising" may mean "one", or may also mean "one or more." The use of the term "or" in the claims is used to mean "and/or" unless explicitly indicated to refer to alternatives only or the alternatives are mutually exclusive, although the disclosures supports a definition that refers to only alternatives and "and/or."

The methods and systems disclosed and claimed herein can be made and executed without undue experimentation based on the level of disclosure presented. While the methods and systems have been described in terms of their preferred embodiments, it will be apparent to those skilled in the art that they are not limited to the exact steps described and may vary from such description without departing from the scope and spirit of the invention. The substitutes and modifications employed by one skilled in the art are deemed to fall within the scope of the invention.

REFERENCES

Klein E, Smith D L, Laxminarayan R (2007). "Hospitalizations and Deaths Caused by Methicilllin-resistant *Staphylococcus aureus* clones in the community". *J Clin Microbiol* 40 (11):4289-94.

Rutala, William A., and Weber, David J. 2008. Guideline for Disinfection and Sterilization in Healthcare Facilities, 2008. CDC.

What is claimed is:

1. A method for reducing microorganism population on a non-food object, said method comprising the steps of:
    placing said object in a chamber, said chamber having
        at least one magnetron,
        at least one waveguide,
        a power supply, and
        controls;
    determining a pulse period and a pulse duration applicable to the desired level of microorganism reduction;
    calculating one or more duty cycles and one or more duty cycle frequencies from the pulse period and the pulse duration applicable to the desired level of microorganism reduction;
    programming said controls accordingly; and
    exposing said object to microwave radiation corresponding to the calculated duty cycles and duty cycle frequencies.

2. The method of claim 1 wherein the one or more duty cycle values range from a fraction to one.

3. The method of claim 1 wherein the one or more duty cycle frequency values range from 10 kHz to a milli Hz.

4. The method of claim 1 wherein the chamber further comprises a generally hollow variable speed tumbler drum in which to place the object.

5. The method of claim 1 wherein the chamber further comprises a raised stationary platform on which to place the object.

6. The method of claim 1 wherein the chamber further comprises a conveyor belt for transporting an object through the chamber during radiation.

7. The method of claim 1 wherein the waveguide is telescoping.

8. The method of claim 1 wherein the waveguide further comprises a slotted radiator.

9. The method of claim 1 wherein the microwave radiation comprises one or more wavelengths between 915 MHz and 300 GHz.

10. The method of claim 1 wherein the microwave radiation comprises one or more wavelengths of about 2.45 GHz.

11. The method of claim 1 wherein the non-food object is selected from the group consisting of:
    linens, towels, washcloths, rags, clothing, shoes, instruments, carpet, fabric, cloth, wood, plastic, glass, synthetic materials, paper, nutritional supplements, botanicals, herbal medicines, plants, minerals, oils, composite materials, building materials, fibers and upholstery.

12. The method of claim 1 wherein the microorganisms are Gram-positive bacterium.

13. The method of claim 1 wherein the microorganisms are Gram-negative bacterium.

14. The method of claim 1 wherein the microorganisms are selected from the group consisting of molds, prions and viruses.

15. A method for reducing a microorganism population on a food object, said method comprising the steps of:
   placing said object in a chamber, said chamber having
      at least one magnetron,
      at least one waveguide,
      a power supply, and
      controls;
   determining a pulse period and a pulse duration applicable to the desired level of microorganism reduction;
   calculating one or more duty cycles and one or more duty cycle frequencies from the pulse period and the pulse duration applicable to the desired level of microorganism reduction;
   programming said controls accordingly; and
   exposing said object to microwave radiation corresponding to the calculated duty cycles and duty cycle frequencies.

16. The method of claim 15 wherein the one or more duty cycle values range from a fraction to one.

17. The method of claim 15 wherein the one or more duty cycle frequency values range from 10 kHz to a milli Hz.

18. The method of claim 15 wherein the chamber further comprises a generally hollow variable speed tumbler drum in which to place the object.

19. The method of claim 15 wherein the chamber further comprises a raised stationary platform on which to place the object.

20. The method of claim 15 wherein the chamber further comprises a conveyor belt for transporting an object through the chamber during radiation.

21. The method of claim 15 wherein the waveguide is telescoping.

22. The method of claim 15 wherein the waveguide further comprises a slotted radiator.

23. The method of claim 15 wherein the microwave radiation comprises one or more wavelengths between 915 MHz and 300 GHz.

24. The method of claim 15 wherein the microwave radiation comprises one or more wavelengths about 2.45 GHz.

25. The method of claim 15 wherein the microorganisms are Gram-positive bacterium.

26. The method of claim 15 wherein the microorganisms are Gram-negative bacterium.

27. The method of claim 15 wherein the microorganisms are selected from the group consisting of molds, prions and viruses.

28. The method of claim 15 wherein the food object is selected from the group consisting of:
   fruits, vegetables, breads, meats, dairy products, spices, powders, crackers, liquids, plants, herbs, juice, extracts, oils, medicines, water, beverages, seafood, yogurt, nuts, seeds, honey, sugar, cereals, grains, jellies, processed foods, eggs and animal foods.

29. A method for destruction of live microorganisms on an object, said method comprising the steps of:
   providing a chamber comprising at least one magnetron, at least one waveguide, a power supply, and a control panel;
   determining a pulse period and a pulse duration applicable to the desired level of microorganism reduction;
   placing the object in the chamber;
   exposing the object to repetitive pulses of microwave radiation for the pulse period and the pulse duration, wherein the pulse duration ranges from a fraction of a second to multiple seconds; and
   employing at least one method to increase signal homogeneity selected from the group consisting of:
   using a telescoping waveguide;
   using a slot radiator;
   using a raised platform on which to place the object;
   using a tumbler drum to mobilize the object;
   using a conveyor belt to mobilize the object; and
   using multiple magnetrons.

30. A method for destruction of live microorganisms on an object comprising the steps of:
   providing a microwave radiation chamber for exposing an object to microwave radiation, wherein the microwave radiation chamber comprises a chamber; at least one magnetron to provide one or more microwave radiation pulses positioned about the chamber, a waveguide positioned in communication with the at least one magnetron, a power supply connected to the at least one magnetron, and a control unit in communication with the power supply and the at least one magnetron, wherein the control unit controls a pulse period and a pulse duration for the one or more microwave radiation pulses;
   determining the pulse period and the pulse duration applicable to the desired level of microorganism reduction; and
   delivering one or more microwave radiation pulses for the pulse period and the pulse duration, wherein the pulse duration ranges from a fraction of a second to multiple seconds.

31. The method of claim 30, further comprising the step of adjusting a microwave mode distribution by providing and adjusting a telescoping waveguide, providing a slot radiator in communication with the waveguide or a combination thereof.

32. The method of claim 31, wherein the providing a slot radiator includes 3, 4, 5, 6, 7, 8, 9, 10, 11, or 12 slots.

33. The method of claim 30, wherein the at least one magnetron comprises at least 2 magnetrons and the at least 2 magnetrons are positioned about a different location of the chamber.

34. The method of claim 30, wherein the object comprises water.

* * * * *